United States Patent [19]

Caimi

[11] Patent Number: 4,724,314
[45] Date of Patent: Feb. 9, 1988

[54] MATERIAL CHARACTERISTICS MEASURING METHODS AND DEVICES

[75] Inventor: Frank M. Caimi, Vero Beach, Fla.

[73] Assignee: Harbor Branch Oceanographic Institution Inc., Ft. Pierce, Fla.

[21] Appl. No.: 898,582

[22] Filed: Aug. 21, 1986

[51] Int. Cl.⁴ ............................................... H01S 3/13
[52] U.S. Cl. ..................... 250/205; 372/29; 372/31; 372/32
[58] Field of Search .................. 250/204, 205; 372/29, 372/31–32, 34

[56] References Cited

U.S. PATENT DOCUMENTS

| 4,092,530 | 5/1978 | Wise | 250/205 |
| 4,369,525 | 1/1983 | Breton et al. | 372/29 |
| 4,410,992 | 10/1983 | Javan | 372/32 |
| 4,632,552 | 12/1986 | Olsson et al. | 250/205 |
| 4,677,632 | 6/1987 | Lisco et al. | 372/31 |

Primary Examiner—Edward P. Westin
Assistant Examiner—Khaled Shami
Attorney, Agent, or Firm—Carroll F. Palmer

[57] ABSTRACT

Radiation from coupled-cavity lasers is used to measure certain characteristics of materials, e.g., absorption, reflectance and other complex dielectric constants of solids, liquids and gases. Novel laser systems with electronic feedback loops are disclosed which provide compensation for laser changes with moderate temperature variations resulting in improved measurement accuracy without adversely affecting system power efficiency. In a preferred embodiment, the invention is used in the measurement of optical attenuance in submarine water over long path-lengths and at relatively specific wavelengths, e.g., about 800 nm.

11 Claims, 12 Drawing Figures

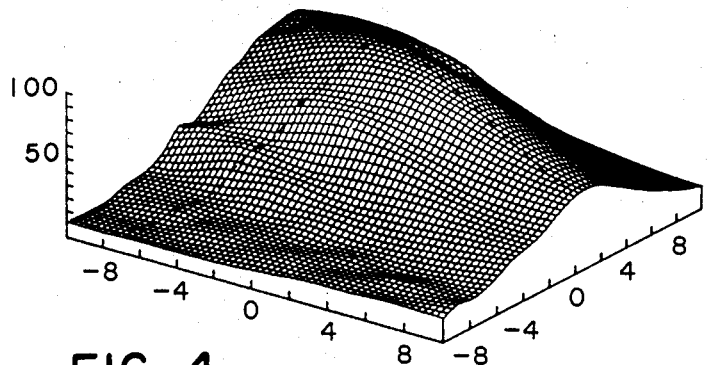
FIG. 4
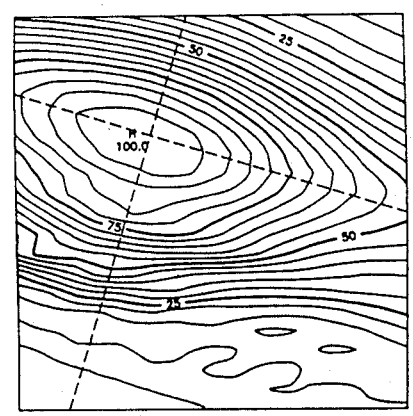
FIG. 6
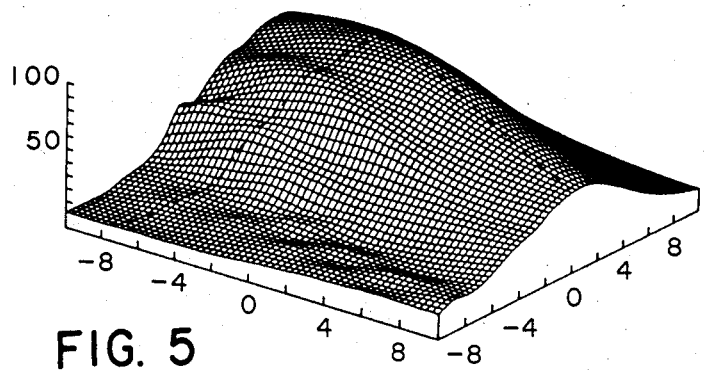
FIG. 5
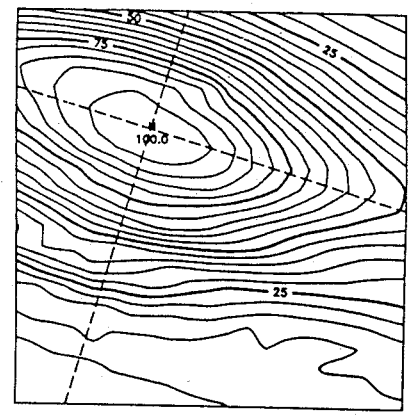
FIG. 7
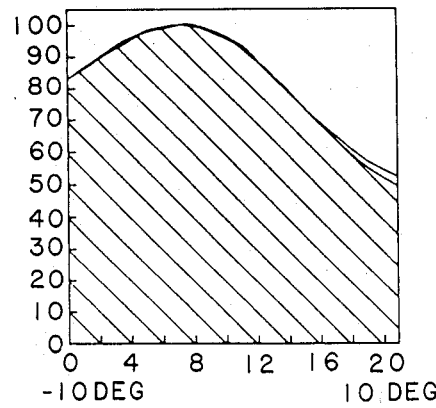
FIG. 8  ☐ TEMP = 23.7°C  ▨ TEMP = 34.5°C
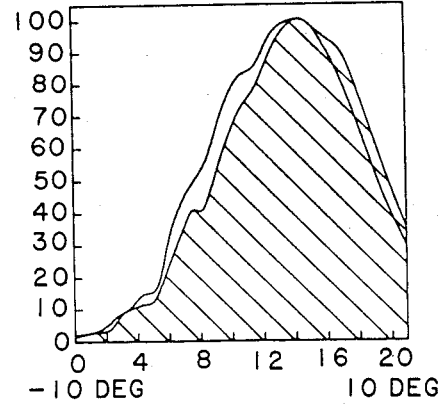
FIG. 9  ☐ TEMP. = 23.7°C  ▨ TEMP = 34.5°C

MATERIAL CHARACTERISTICS MEASURING METHODS AND DEVICES

BACKGROUND OF THE INVENTION

1. Field of the Invention

This invention relates to the measurement of physical values, such as absorption, reflectance, attentuance, scatterance, etc., of materials by imposing laser radiations on the material and detecting radiations emitting from such radiated material. More particularly, it concerns use of coupled-cavity lasers combined with electronic feedback circuits to provide wavelength and radiance control in the lasers as the radiation source in performing such laser radiation measurements.

2. Description of the Prior Art

Optical techniques for the measurement of a wide variety of material characteristics are extensively used in industry, research, or elsewhere to determine the physical values of materials under test. Spectrometry methods and apparatus for determination of optical absorption, attenuance, scatterance and other values of gases, liquids and solids is a typical example of such optical techniques.

Typical methods of measurement for optical absorption in transparent material are by conventional transmission, interferometry, laser intercavity absorption, photothermal detection, photoacoustic calorimetry and thermal lens calorimetry. The relative merits of these different methods have been adequately discussed in the literature (T.D. Harris, etal., Proceeding of SPIE, Vol. 426, pg. 110 T.D. Harris, Anal. Chem. 54, 1982). The present invention relates to transmission-sensitive type methods for among the full spectrum of methods available.

Such measurement operations often require highly collimated (parallel) radiation beams to attain accuracy in measurement values and propagation over long test paths. Lasers of various wavelengths and types have been used in the past in performing such measurements, e.g., study of trace materials (pollutants) in the atmosphere and elsewhere. Semiconductor (diode) lasers offer advantages in such procedures due to their small size and high conversion efficiency. However, such lasers suffer from several distinct problems, i.e., (a) emitted wavelength varies with temperature and excitation current and (b) emitted radiant flux varies substantially with emitter temperature. Methods have been proposed for correction of these defects including (1) wavelength stabilization by temperature control [L. W. Chaney, etal., Appl. Opt. 18, Sept., 17 1979], (2) wavelength stabilization by combined temperature and current control [R. A. Keller, Proc.SPIE, Vol. 426, 1983], (3) radianco stabilization by optical feedback [Amada, J. of Q.E. QE 19, Sept., 9 1983], (4) radiance stablization by synchronously modulation of beams by electro-optical feedback [Caimi, etal. Proc. SPIE Ocean Optics VII: 489, 1985], etc.

In addition to the above listed problems, well known characteristics of solid-state laser diodes predicate use of complicated bias and modulation methods to avoid facet damage and operation below threshold over temperature extremes. Although temperature control of the laser emitter is possible to eliminate these problems and provide mode stabilization, system power efficiency is compromised.

Sources of inaccuracy in measurements using prior art laser methods and devices include:

A. The laser threshold current and differential efficiency decrease with inceasing temperature and age.

B. Diode lasers can vary in wavelength while maintaining a single longitudinal mode at a bias somewhat above threshold. As temperatue increases, each longitudinal mode shifts to longer wavelengths as a result of refractive index changes.

C. Asymetric aging of front and rear facets can cause long term output radiance changes in systems deriving radiance feedback from the alternate facet.

D. The near field radiation pattern can become spotty with age. Angular changes in the far-field may result.

E. Transverse/lateral mode changes can result depending upon device structure, temperature and current.

F. Bandgap temperature dependence in any photodetector results in responsivity changes to the detected energy.

The present invention makes possible the mitigation of these problems in the optical measurement operations to which the invention is directed.

The recent development of coupled-cavity or distribuited lasers [Tsang, et al. "Semiconductors and Semimetals", Ch. 4, Vol. 22, Academic Press, 1985[ presents some advantage over the previous work cited above since very fine wavelength tuning is possible. Such coupled-cavity lasers were developed for communication systems, but in accordance with the present invention are applied with added improvements to spectrometry and comparable optical measurements. In addition, a utility of this invention is the application of cavity-tuned lasers, e.q., coupled-cavity lasers, to spectrometry of either broad or narrow absorbing test species.

OBJECTS

A principal object of the invention is provision of new optical methods and devices for the measurement of physical values such as absorption, reflectance, attentuance, to scatterance, etc. of gases, liquids and solids.

Further objects include the provision of:

1. Improvements in optical measurement techniques by imposing controlled laser radiations on test materials and detecting radiations emitting from such radiated material.

2. Wavelength control in laser radiations in such optical measurements through electrical feedback to an element of the laser cavity while maintaining simultaneous electrical feedback for stabilization of the output radiance by control of the laser current.

3. Auto-zero circuitry in the laser radiation devices to null the detector output for variation in reference and sensing optical paths.

4. New laser radiation methods and devices having the ability to make spectral measurement at very precise wavelengths without need for precise temperature control of the laser.

5. Such methods and devices that are adaptable to optical fiber measurement operations, e.g., operations in which optical fibers are used for most or all optical paths.

6. Such methods and devices useable in environments where ambient lighting or other optical noise sources are mitigated as possible contaminates to the measurement results.

7. Such measurement devices that do not require mechanically moving parts, e.g., mechanical choppers, motors, etc.

8. Compensations in such optical measurements to mitigate changes in far-field radiance distribution or wavelength division operations or optical paths due to temperature changes or element aging.

9. Reduction of temperature coefficient effects from optical detectors by time division multiplexing reference and signal beam originating from the same source thereby eliminating calbration problems relating to source aging and/or use of moving mechanical parts.

10. Maintenance in such optical measurement operations of wavelength stability over a broader temperature range than has been possible heretofore with other laser based measurement systems.

11. Such improved optical measurement methods that can be used with both single and double path measurement procedures.

12. New laser methods and devices for measurement of optical attenuance, absorption or scattering function through a medium having large absorption profile width, e.g., sea water, compensated for temperature-induced longitudinal mode shifts of the laser.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The objects are accomplished, in part, in accordance with the invention by utilization of the inherent advantages of coupled-cavity laser structures, i.e., tunability and wavelength/longitudinal mode stability, in combination with additional temperature and radiance stabilization improvements to achieve new optical measurement methods and devices of unique accuracy and simplicity.

Basically the invention involves the use of three electronic feedback control loops in coupled-cavity lasers, i.e., a wavelength loop, an intensity loop and a null (auto-zero) loop, to achieve wavelength and radiance stabilization over a range of temperature and other ambient condition variations.

In the wavelength control loop, two control inputs are applied simultaneously. One input is derived from a high frequency oscillation ($\omega_1$) and is applied to a modulator diode of the laser. Thus, the output wavelength of the coupled-cavity laser is modulated at an $\omega_1$ rate and at small amplitude. Because the output radiance of the laser is non-linearly related to the modulator current, these small amplitude-induced current variation produce an intensity derived signal from the synchronous detection circuit in proportion to the deviation from optimal current for a given longitudinal mode.

The second input to the wavelength control loop is a square wave or equivalent signal at a much lower oscillation frequency ($\omega_o$). Thus, different longitudinal modes (different wavelengths) are selected during each half-wave of the square wave signal.

The success of the invention is due, in part, on the use in combination, as desirable features, of collimated emission of the test material radiation and ambient light rejection by synchronous detection. A steady state average (bias) radiant output to the test material is controlled by feedback from a monitoring detector, while modulation about that bias is maintained and stabilized by separate feedback from a synchronous detector.

BRIEF DESCRIPTION OF THE DRAWINGS

A more complete understanding of the invention may be had by reference to the accompanying drawings in which:

FIG. 4 is a far-field 3-D representation of measured radiant intensity with a seim-conductor laser system in accordance with the present invention with an approximately 0.5×2 um emitting area when at a temperature of 23.7° C.

FIG. 5 is a far-field 3-D representation of measured radiant intensity with the laser system of FIG. 4 when at a temperature of 34.5° C.

FIG. 6 is a contour plot of the far-field data of FIG. 4.

FIG. 7 is a contour plot of the far-field data of FIG. 5.

FIG. 8 is a cross-sectional scan of the far-field data of FIG. 4 corresponding to the 0.5 um facet dimension.

FIG. 9 is a cross-sectional scan of the far-field data of FIG. 4 corresponding to the 2 um facet dimension.

DESCRIPTION OF THE PREFERRED EMBODIMENTS

Figure 1A:
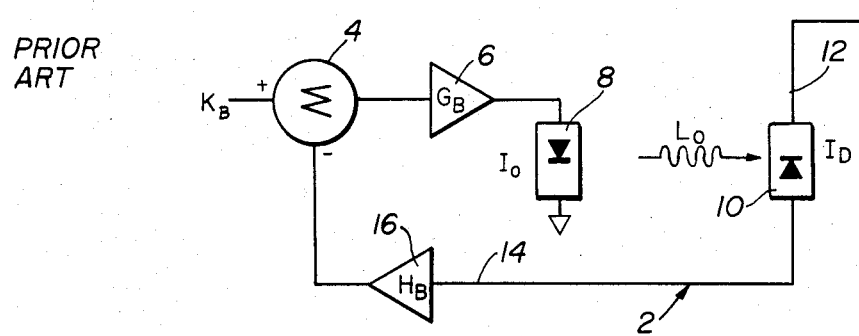
FIGS. 1a and 1b are schematic diagrams of prior art simultaneous feedback systems used to stabilize diode laser radiation output relative to ambient temperature variations.
Figure 1B:
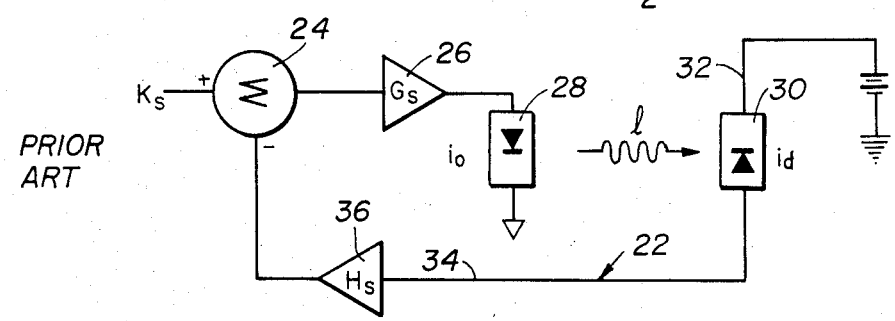
Figure 2:
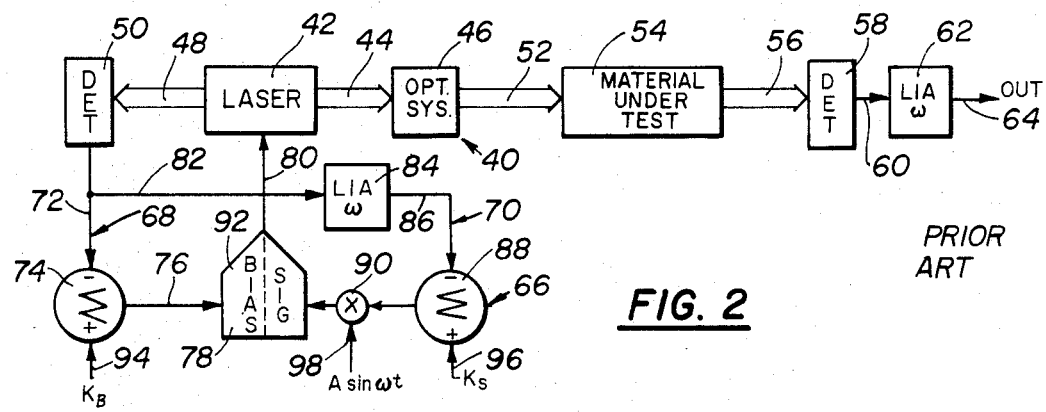
FIG. 2 is a schematic diagram of a conventional, prior art semiconductor laser optical transmittance measurement system.

Referring in detail to the drawings, in which identical parts are identically marked, several laser feedback schemes used in the prior art are shown in FIGS. 1a 1b and 2. Thus, FIG. 1a showns a typical zero type control loop having $K_b$ as an input and any parameter which is a function of dc bias as the control parameter. In the loop 2, the d.c. input $K_B$ is fed to the algebraic summer 4 and passes via the gain amplifier 6 to the laser 8 causing it to emit the light flux $L_o$ to the photodetector 10. With the detector diode 10 connected to zero or positive voltage 11 via connection 12, its output loops via conductor 14 and gain amplifier 16 back to summer 4. The resulting operation may be expressed by the formula: $L_o = (I_o)$, $I_o = g[L, \lambda(I_o), T]$, where $\lambda$ is wavelength as a mathematical function dependent upon $I_o$, $I_o$ is the bias current to the laser, L is radiant flux, $\omega$ is frequency, g is a mathematical function characteristic of the particular semi-conductor laser construction and detection geometry and T is temperature.

In FIG. 1b, the loop 22 uses a time varying signal as input $K_S$. The a.c. input $K_S$ is fed to the algebraic summer 24 and passes via the gain amplifier 26 to the laser 28 causing it to emit the light flux 1 to the photodetector 30. With the detector diode 30 connected to zero or positive voltage 11 via connection 32, its output loops via conductor 34 and gain amplifier 36 back to summer 24. The resulting operation may be expressed by the formula: $l=f(i_o)$, $i_d=g[l,\lambda(I_o),T]$, where $\lambda$ is wavelength, l is the ac component of radiant flux, f is frequency, g is a mathematical function characteristic of the particular semi-conductor laser construction and detection geometry and T is temperature.

If $K_S$ is of nearly zero mean amplitude and spectrally removed from the response band of loop 22, then a degree of independence can be observed between the loops 2 and 22. Typically, the control parameter in loop 2 would be a laser diode's average radiant output, while the control parameter in loop 22 would be a synchronously detected a.c. component of the radiant output. In this way, variation of the L and l values (due to changes in $i_{th}$) are compensated to avert facet damage at low temperature and avert spectral broadening at high temperature where the threshold condition may not be met. Similar schemes have been disclosed to achieve radiance stabilization of ±several percent over a 50° C. range and over the lifetime of the laser.

Another method can be used to effect wavelength stabilization (over perhaps 10° C.) while also maintaining constant a.c. modulated output radiance. For this, loop 2 is given a control signal derived from a wavelength sensing device, e.g., grating. Loop 22 is used for detection of optical absorption. In any event, when optical transitions are narrow, frequency/amplitude stabilization techniques are common and result in acceptable accuracy of measurement, but the accuracy in such prior art techniques have been unacceptable where optical transitions are wide.

FIG. 2 represents a known semiconductor transmittance measurement system combining two loops as illustrated in FIGS. 1a and 1b as a feedback system providing a double loop bias/small signal radiance compensator.

In FIG. 2, the optical measurement system 40 comprises laser 42 connected via light path 44 to optical system 46, e.g., tandem lens arrangement, and via light path 48 to feedback control detector 50. The radiation output from system 46 passes via light path 52 to the material 54 under test and the radiation emitted (transmitted or reflected) from material 54 passes via light path 56 to photodetector 58 which inputs a signal via lead 60 to lock-in-amplifier (LIA) 62 which, in turn, passes a signal via lead 64 to a measurement unit (not shown), e.g., a calibrated meter. Typically, detector 58 will be identical to detector 50.

The radiance compensator portion 66 of system 40 comprises the bias loop 68 and the signal loop 70. The loop 68 includes lead 72 from feedback control detector 50 to summer 74, lead 76 to bias amplifier 78 and lead 80.

The loop 70 includes lead 82 to the LIA 84, lead 86 to the summer 88, junction 90, signal amplifier 92 and lead 80.

The dc bias $K_B$ is applied to summer 74 via input 94, dc signal $K_S$ controlling the ac radiance component is applied to summer 88 via input 96 and the ac signal at frequency $_1$ is applied to multipler junction 90 via the input 98 to provide ac modulation of the laser current via amplifier 92 in proportion to the error signal from summer 66.

Typical known single mode lasers exhibit mode hopping both with bias current and temperature change on the order of 0.2–0.5 nm/° C. and roughly 0.2 nm/mA. Residual temperature coefficients of about 0.1–0.2 nm/° C. can be compensated by adding a carrier injection tuning mechanism to the laser structure. Typically, a 4 Å shift can be induced with an injection current of 4 mA. Greater tuning range has been demonstrated for cleaved-coupled-cavity ($C^3$) lasers. As a result of the present invention, it has been discovered that the greater tuning control available in $C^3$ lasers allows a two loop feedback method to be used with this class of laser to create uniquely improved material characteristics measurement instrumentation.

Figure 3:
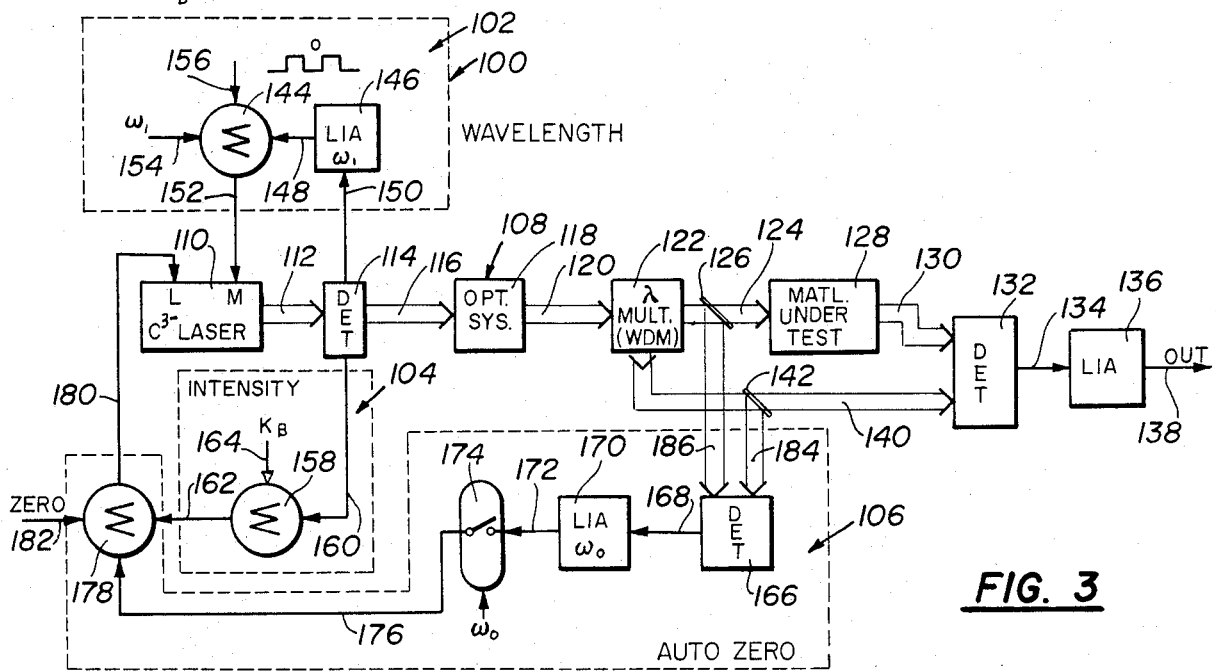
FIG. 3 is a schematic diagram of a coupled-cavity laser optical measurement system structured in accordance with the present invention.

An embodiment of a three control loop laser optical measurement system of the present invention is shown in FIG. 3. In this system, a coupled-cavity laser is used in the wavelength tunable mode (one diode biased above and one biased below threshold).

The laser system 100 of the invention comprises a wavelength control loop 102, an intensity control loop 104, an auto-zero loop 106 and the optical measurement unit 108.

The basic elements of unit 108 include the coupled-cavity laser 110, light path 112, control detector 114, light path 116, optical system 118, light path 120, wavelength-division-multiplexor (WDM) 122, light path 124 having a beam-splitter semi-mirror 126, test material holding section 128, light path 130, photodector 132, lead 134, LIA 136, measurement signal output 138 and light path 140 with its beam-splitter semi-mirror 142. Some of the light paths, e.g., 112, may be integral transparent junctions between elements. More typically, they may be a series of lenses, fiber optics, etc.

The wavelength control loop 102 comprises summer 144, LIA 146, leads 148, 150, and 152 and inputs 154 and 156.

The intensity control loop 104 comprises summer 158, leads 160 and 162 and input 164.

The auto-zero loop comprises photodector 166, lead 168, LIA 170, lead 172, electronic switch 174, lead 176, summer 178, lead 180, input 182 and light paths 184 & 186.

In operation of the device 100, wavelength control of the radiation from laser 110 to light path 112 is achieved via control loop 102 using an ac signal $\omega_1$ from a high frequency oscillator (not shown) applied to input 154 and a square-wave signal $\omega_o$ applied to input 156. The control signal generated by the summer 144 is applied to the modulator diode M via lead 152 which exhibits non-linearity of output power versus modulator current.

An oscillator signal is also applied to summer 144 via lead 148 from LIA controlled by an intensity derived signal from the synchronous detector 114/146 which responds in proportion to the deviation from optimal current for a given longitudinal mode of the laser 110. By control of the dc input to the loop via 156, different longitudinal modes may be selected. In addition, since laser amplitude modulation is allowed under these conditions use of the auto-zero capability 106 is made possible. The bias input $\omega_o$ to input 156 is driven at a much lower frequency compared to $\omega_1$ input 154 thereby alternatively switching the output wavelength of the laser 110 at an $\omega_o$ rate. The WDM 122 switches the laser output via 112 ... 120 between the light paths 124 and 140 at the $\omega_o$ rate.

The path 124 involves the material 128 under test and the path 140 serves as a reference.

Advantageously, detectors 132 and 166 are a pair of matched, separate detectors at the same temperature, one to receive the test path signal and the other the reference path signal. Detector 132 responds to differences in signal proportional to the absorption of the test material, while the other 166 responds to unwanted absorption changes between the reference and test paths arising from (1) lateral/transverse mode changes of the laser affecting radiant flux coupling between the laser 110 and the detectors 132, 166, (2) optical radiant flux variations in the WDM 122 of paths 124, 130, 140 due to temperature changes or (3) any wavelength dependent mechanism affecting radiant flux transfer between the reference 140, 184 and signal paths 124, 130.

FIGS. 4-11 serve to illustrate improvements in wavelength and radiance stabilization in cavity-coupled lasers versus ambient temperature changes and in laser radiation material measurement operations attained by way of the present invention. In the following description of the gathering of the data, the number in () following a system element, e.g., a laser, relate that element corresponding numbered elements in FIG. 3.

A series of experiments were conducted to obtain data on the short term stability of radiance output of a $C^3$ laser versus temperature change using a TJS GaAlAs type laser (110) [commercially available as a Mitsubishi ML3101 diode] operating integral with a UDT silicon detector (114) at 800 nm. These elements were mounted in an insulated, temperature-controlled (0.1° C.) silicon oil bath which was stirred constantly. To eliminate interference effects and temperature dependent back-reflections (phase changes) which might couple to the laser cavity, the laser window was removed. The optical path was kept clear in the mechanical design.

Two-dimensional scans of far-field intensity patterns were conducted over most of the major lobe at temperatures of 23.7° C. and 34.5° C. Anomolies in the far-field intensity patterns were observed as a function of average injection current and/or temperature by lock-in detection of a 1 kHz modulating signal at 40% modulation. Feedback stabilization was implemented, as it would be in conventional transmission spectrometry and feedback parameters were monitored.

Data recorded by these operations are shown isometrically in FIGS. 4 and 5. Contour plots and cross-sectional plots of the data are shown in FIGS. 6-9.

Figure 10:
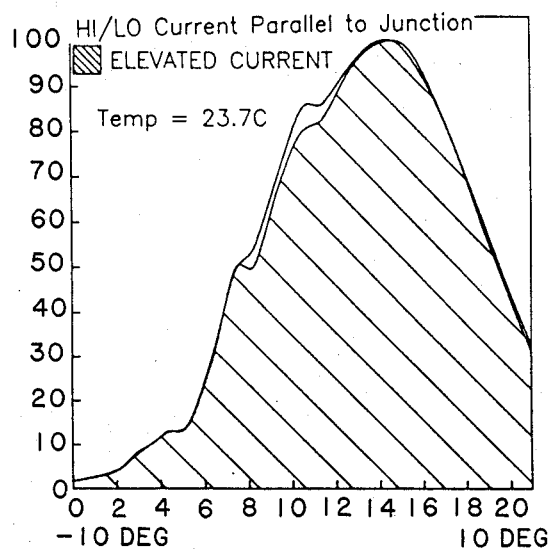
FIG. 10 is a cross-sectional intensity map of far-field data at two operating current levels with the elevated current adjusted to the value assumed by the feedback controller at elevated temperature (30.4° C).

During the above described operations, the total optical power output from the rear facet of the laser was kept constant within about ±0.2%. Therefore, injection current and temperature increased simultaneously. In an effort to independently determine the effects of temperature and current, additional far-field data were gathered at slightly reduced, but constant ambient temperature while the bias-current was altered to the value the intensity loop (104) required at a higher temperature (30.4° C.). The ambient temperature was reduced slightly to account for increased power dissipation with resulting temperature rise in the laser due to thermal resistance. Cross-sectional plots of the resulting data are shown in FIG. 10.

It was discovered that mode changes are more significant with temperature change than with current change alone. Changes in current appear to be correlated with low-amplitude, higher order, mode competition. However, changes in temperature in these experiments produce angular emission changes (1°) over a 10° C. temperature change. Elevated current at a constant temperature and elevated temperature tend to reduce the far-field width at levels above 50% of peak intensity. In long-path measurement, variation of the wavefront curvature can result in significant error due to tracking misalignment or detector response changes over the active area.

Another experiment was performed to further study the thermal behavior of the far-field. The integrally mounted detector diode (114) was again used to provide the feedback signals from the laser (110) rear facet. An externally mounted 1 cm diameter detector, operating within its linearlity range, was used to synchronously detect a portion (±5 acceptance cone) of the flux from the front facet of the laser while temperature was varied. Plots of the resulting bias (d.c. error), a.c. error and detected output data are presented in FIG. 11. The output shows periodic oscillation (6.7° C.) about an average negative slope of about 0.15%/° C. corresponding to the temperature coefficient of response ($R_T$) of the internally mounted detector (114). The magnitude of the oscillation (3%) limits the measurement accuracy obtainable when temperature is not known.

Figure 11:
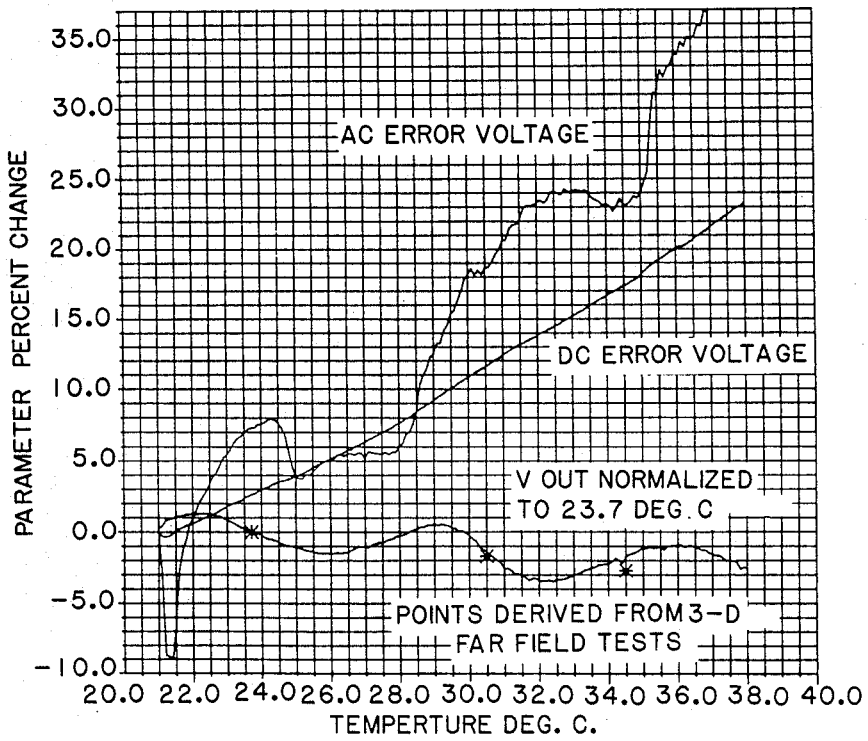
FIG. 11 is a graph showing percentage change of d.c. and a.c. error voltage for feedback control as with systems shown in FIGS. 1a, 1b and 2 and sychronously detected output ($\pm 5°$ cone) for front facet emission of the laser. This is compared with data of the 3-D far-field tests ($\pm 5°$ cone) at front facet with a laser of the present invention shown to indicate degree of tracking between front/rear facets.

Additional points derived from the 3-dimensional plots of FIGS. 4 and 5 were added to FIG. 11 at the three temperatures shown. These data were computed by integrating the far-field data over a ±5° cone and normalizing these values to integrated data at angles subtended by the internally mounted detector. The data agreement show that the tracking between front and rear facets is good. This was substantiated by using an alternate feedback detector/beam-splitter arrangement about the front facet. The periodic variation remained, however, being indicative of periodic changes in shape of the far-field with temperature. This indicates the need in using identical f-number optics, e.g., in optical systems 108, 112, 116, 120, 124, 130, 140, 184 and 186 in the detection and feedback control optical paths in instrumentations of the invention.

In specific embodiments of the invention, cleaved-cavity-coupled ($C^3$) lasers are advantageously used as the cavity-coupled lasers (110).

By way of example of components useable in specific embodiments, lock-in amplifiers (146, 136, 170) may be commercially available units from the Princeton Applied Research division of EG&G, Analog Devices AD 630 or two inverting amplifiers, a MOSFET SPDT switch and a filter amplifier. A coupled-cavity semiconductor laser structure (110) using a GaAlAs heterostructure device, e.g., ML3101, coupled with an external cavity may be used. Such external cavity can consist of two duplicate lasers in close proximity, e.g., 1 mm., to each other and aligned with parallel facets. Alternate Fabry-Perot or other interferometric cavities can also be used in place of one laser. In these latter configurations, it is necessary to utilize electrooptic modulators to vary the cavity tuning via the input in FIG. 3.

Detector (114) should be sensitive to the wavelength emitted by the laser. Silicon PN or PIN detectors available from EG&G or United Detector will serve in the spectral region from the visible wavelengths to near 1 $\mu$m.

The optical system (108) can consist of a graded index optical element (Galileo Electrooptics) for connection to the fiberoptic cables (Corning Glass) (112, 116, 120, 124, 140, 130, 184, 186). Wavelength Division Multiplexor (122) may be a grating, internal reflection element, or filter type depending upon the degree of wavelength shift induced by the signal $\omega_o$. These WDMs are commercially available from Microcoatings, Inc.

Dectors 132 and 136 may be pyroelectric types (Eltec, Inc.) silicon, germanium or a variety of known infrared types (Infrared Industries).

Switch (174) may be constructed from a MOSFET or other electric switch such as the RCA CD 4053. Summers (144, 158, 178) may be constructed from operational amplifiers (National LF 411) and others. Resistor network summing junctions may also be used.

The clock signals may be generated using laboratory-type signal generators or CMOS crystal controlled oscillator/dividers. Typical valsue for $\omega_o$ are $2 \times 100$ Hz or less and for $\omega_1$, much greater than $2 \times 10,000$ Hz.

In an application of the invention near 800 nm in air, a 0.5 cm diameter collimated laser output beam was separated into two separate paths by reflection from a Bausch & Lomb diffraction grating (WDM). The beams were recombined onto a 1 cm. diameter silicon detector (UDT Pin10DP) and detected by a laboratory constructed LIA operating at a frequency of 1 KHz. Optical absorption in the test path was induced by inserting a water sample into it and the resulting change in values from the detector was recorded. Signals derived from a beam splitter in both paths were used to compensate for variations of the transmitted light between both paths and constituted the auto-zero function. The auto-zero loop used a similar detection system to the one just described. The temperature of the laser diode was altered by heating an electical resistance in the laser collimating mount assembly over a 10° C. temperature range and resulting changes in values from the detector were recorded.

In another test, a microscopic cover glass was used as a test material sample. The Fresnel loss due to reflection was adequately measured as a loss in the test beam.

The data acquired as a result of the above procedures showed that the detection output variations due to the temperature change were reduced by less than 1/10th by the use of the auto-zero loop as compared to detection output without such loop in operation.

The embodiments of the invention in which an exclusive property of privilege is clained are defined as follows:

1. A device for the measurement of physical characteristics of test materials by subjecting the test material to radiation from a coupled-cavity laser and detecting changes in radiation emitting from said material resulting therefrom as compared to the incident radiation which comprises:
   means to divide the radiation beam from said laser into a material test path and a reference path,
   a detector to evaluate wavelength and intensity differences in said test path and said reference path after said test path has encountered said test material,
   a radiation intensity loop controlling the output of said laser,
   a radiation wavelength loop controlling the output of said laser, and
   an auto-zero loop to stabilize the radiation output of said laser against wavelength and intensity changes which would otherwise occur in said radiation output with changes in the temperature of said laser in the absence of said auto-zero loop.

2. The device of claim 1 wherein said auto-zero loop comprises:
   a summer that receives an input signal from said intensity loop and delivers an output signal to said laser,
   a detector which receives a portion of said radiation in said test path before encounter with said test material and said reference path,
   a lock-in amplifier to receive an signal from said auto-zero loop detector, and
   an electronic switch to interrupt a signal passing from said lock-in amplifier to said summer.

3. The device of claim 2 wherein said means to divide is a diffraction grating.

4. The device of claim 3 wherein said wavelength loop comprises:
   a summer to deliver an input signal to said laser,
   a square-wave signal input to said summer,
   a high frequency signal input to said summer, and
   a lock-in amplifier to supply an input signal to said summer.

5. A device to measure physical characteristics of test materials by subjecting the test material to radiation from a coupled-cavity laser and detecting changes in radiation emitting from said material resulting therefrom as compared to the incident radiation which comprises:
   a coupled-cavity semiconductor laser to project a radiation beam,
   means to separate said beam into a test path and a reference path in response to wavelength modulation of said laser at a predetermined rate $\omega_o$ and
   detection means by which said test and reference paths are compared alternately at rate $\omega_o$ as a result of said wavelength modulation.

6. The device of claim 5 which includes:
   feedback means for comparison of said the beams in said teeth path and said reference path prior to encounter of said test path with said test material,
   a detector combined with said feedback means which may be nulled automatically in response to imbalance in said test path and said reference path occurring from temperature related effects in said laser.

7. The device of claim 5 which includes means for stabilizing the longitudinal mode of said laser emission in response to modulation of said laser at a rate $\omega_1$ substantially higher in frequency than the simultaneously applied modulation at said rate $\omega_o$.

8. The device of claim 7 which includes means to stabilize said laser emission in response to output efficiency variations caused by temperature changes or aging.

9. A device for the measurement of physical characteristics of test materials by subjecting the test material to radiation from a coupled-cavity laser and detecting changes in radiation emitting from said material resulting therefrom as compared to the incident radiation which comprises:
   means to divide the radiation beam from said laser into a material test path and a reference path,
   a detector to evaluate wavelength and intensity differences in said test path and said reference path after said test path has encountered said test material,
   a radiation intensity loop controlling the output of said laser, a radiation wavelength loop controlling the output of said laser, and an auto-zero loop to stabilize the radiation output of said laser against wavelength and intensity changes which would otherwise occur in said radiation output with changes in the temperature of said laser in the absence of said auto-zero loop.

said auto-zero loop comprising
- a summer that receives an input signal from said intensity loop and delivers an output signal to said laser,
- a detector which receives a portion of said radiation in said test path before encounter with said test material and said reference path,
- a lock-in amplifier to receive an signal from said auto-zero loop detector, and
- an electronic switch to interrupt a signal passing from said lock-in amplifier to said summer. said wavelength loop comprises:
- a summer to deliver an input signal to said laser,
- a square-wave signal input to said summer,
- a high frequency signal input to said summer, and
- a lock-in amplifier to supply an input signal to said summer.

10. The device of claim 9 wherein said means to divide is a diffraction grating.

11. A method for the measurement of physical characteristics of test materials by subjecting the test material to radiation from a coupled-cavity laser and detecting changes in radiation emitting from said material resulting therefrom as compared to the incident radiation which comprises:

dividing the radiation beam from said laser into a material test path and a reference path, evaluating wavelength and intensity differences in said test path and said reference path after said test path has encountered said test material, a automatically controlling the output radiation intensity of said laser, a automatically controlling the radiation wavelength output of said laser, and automatically stabilizing the radiation output of said laser against wavelength and intensity changes which would otherwise occur in said radiation output with changes in the temperature of said laser.

* * * * *